(12) United States Patent
Mark et al.

(10) Patent No.: US 9,387,010 B2
(45) Date of Patent: Jul. 12, 2016

(54) SURGICAL ACCESS ASSEMBLY AND METHOD OF USING SAME

(71) Applicant: Nico Corporation, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 493 days.

(21) Appl. No.: 13/786,062

(22) Filed: Mar. 5, 2013

(65) Prior Publication Data
US 2013/0204287 A1 Aug. 8, 2013

Related U.S. Application Data

(63) Continuation-in-part of application No. 13/280,015, filed on Oct. 24, 2011, which is a continuation-in-part of application No. 11/665,666, filed as application No. PCT/US2005/039185 on Oct. 28, 2005, now abandoned.

(60) Provisional application No. 60/623,094, filed on Oct. 28, 2004.

(51) Int. Cl.
*A61F 11/00* (2006.01)
*A61B 17/34* (2006.01)
(Continued)

(52) U.S. Cl.
CPC ..... *A61B 17/3423* (2013.01); *A61B 17/320016* (2013.01); *A61B 17/3417* (2013.01);
(Continued)

(58) Field of Classification Search
CPC .......... A61B 17/34; A61B 6/03; A61B 5/055; A61B 1/06; A61B 17/3421; A61B 17/3417; A61B 2019/4857; A61B 2019/208; A61B 2019/5217; A61B 8/0808; A61B 2019/462; A61B 17/3205; A61B 5/061; A61B 5/0066; A61B 2019/5251; A61B 8/0841; A61B 5/0071; A61B 6/12; A61B 2017/3456; A61B 8/12; A61B 2019/521; A61M 39/06; A61M 2039/0626
USPC ............................. 600/566–567; 604/164.01; 606/184–185
See application file for complete search history.

(56) References Cited

U.S. PATENT DOCUMENTS 3,690,323 A 9/1972 Wortman et al.
3,825,007 A 7/1974 Rand
(Continued)

FOREIGN PATENT DOCUMENTS

DE 10224005 A1 12/2003
RU 2009124446 A 1/2011
(Continued)

OTHER PUBLICATIONS

PCT International Search Report dated Jul. 24, 2014 for PCT/US2014/015755.
(Continued)

*Primary Examiner* — Amy R Weisberg
(74) *Attorney, Agent, or Firm* — Kristin L. Murphy; Brooks Kushman P.C.

(57) ABSTRACT

A surgical access assembly is described that includes an outer sheath and a selectively removable obturator. The outer sheath is defined by an open distal end and an open proximal end and includes a hollow body portion therebetween. The obturator is defined by a distal end and a proximal end, wherein the distal end further comprises a tapered distal tip member. The obturator is configured to be received within the outer sheath such that the tapered distal tip member protrudes from the open distal end of the outer sheath when the obturator is in an introducing configuration. The outer sheath further includes a gripping member, wherein the gripping member includes at least one retaining notch formed on an outer surface thereof.

18 Claims, 5 Drawing Sheets

(51) Int. Cl.
  *A61B 17/32*  (2006.01)
  *A61M 39/06*  (2006.01)
  *A61B 6/12*  (2006.01)
  *A61B 8/08*  (2006.01)
  *A61B 8/12*  (2006.01)
  *A61B 5/00*  (2006.01)
  *A61B 5/055*  (2006.01)
  *A61B 17/3205*  (2006.01)
  *A61B 1/00*  (2006.01)

(52) U.S. Cl.
  CPC ............ *A61B17/3421* (2013.01); *A61M 39/06* (2013.01); *A61B 1/00154* (2013.01); *A61B 5/0066* (2013.01); *A61B 5/055* (2013.01); *A61B 6/12* (2013.01); *A61B 8/0808* (2013.01); *A61B 8/0841* (2013.01); *A61B 8/12* (2013.01); *A61B 17/3205* (2013.01); *A61B 2017/320064* (2013.01); *A61B 2017/3456* (2013.01); *A61B 2090/103* (2016.02); *A61M 2039/0626* (2013.01)

(56) References Cited

U.S. PATENT DOCUMENTS

| | | | | |
|---|---|---|---|---|
| 4,015,604 | A * | 4/1977 | Csillag | A61F 13/4755 604/365 |
| 4,273,635 | A * | 6/1981 | Beraud | D04H 1/559 204/165 |
| 4,386,602 | A | 6/1983 | Sheldon et al. | |
| 4,477,256 | A * | 10/1984 | Hirsch | 604/362 |
| 4,638,798 | A | 1/1987 | Shelden et al. | |
| 4,655,752 | A | 4/1987 | Honkanen | |
| 4,675,110 | A * | 6/1987 | Fay | A61B 10/0038 210/436 |
| 4,798,591 | A * | 1/1989 | Okada | A61M 25/00 604/170.02 |
| 5,183,464 | A | 2/1993 | Dubrul et al. | |
| 5,217,441 | A | 6/1993 | Shichman | |
| 5,222,487 | A | 6/1993 | Carr et al. | |
| 5,249,568 | A * | 10/1993 | Brefka | A61B 1/31 600/184 |
| 5,295,952 | A * | 3/1994 | Pietrafitta | A61B 10/04 604/1 |
| 5,320,611 | A | 6/1994 | Bonutti et al. | |
| 5,397,311 | A * | 3/1995 | Walker | A61M 25/0668 604/160 |
| 5,417,705 | A * | 5/1995 | Haber | A61B 17/3417 604/164.12 |
| 5,431,638 | A * | 7/1995 | Hennig | A61B 17/3421 128/908 |
| 5,431,676 | A | 7/1995 | Dubrul et al. | |
| 5,487,739 | A | 1/1996 | Aebischer et al. | |
| 5,490,843 | A * | 2/1996 | Hildwein | A61B 17/29 604/164.03 |
| 5,676,689 | A * | 10/1997 | Kensey | A61B 17/0057 604/168.01 |
| 5,716,369 | A * | 2/1998 | Riza | A61B 17/0469 606/139 |
| 5,728,132 | A | 3/1998 | Van Tassel et al. | |
| 5,735,865 | A * | 4/1998 | Schaumann | A61B 1/317 600/101 |
| 5,772,678 | A * | 6/1998 | Thomason | A61B 17/3417 604/164.1 |
| 5,860,996 | A | 1/1999 | Urban et al. | |
| 5,967,970 | A | 10/1999 | Cowan et al. | |
| 5,989,228 | A * | 11/1999 | Danks | A61B 17/3496 251/149.1 |
| 6,010,531 | A * | 1/2000 | Donlon | A61B 17/00234 623/2.1 |
| 6,047,218 | A | 4/2000 | Whayne et al. | |
| 6,052,184 | A * | 4/2000 | Reed | G01N 15/0211 356/337 |
| 6,123,667 | A * | 9/2000 | Poff | A61B 17/0218 600/201 |
| 6,129,685 | A | 10/2000 | Howard, III | |
| D434,148 | S * | 11/2000 | Sauer | D24/140 |
| 6,179,826 | B1 * | 1/2001 | Aebischer | A61F 2/022 424/570 |
| 6,224,608 | B1 * | 5/2001 | Ciccolella | A61B 17/3421 604/115 |
| 6,226,548 | B1 | 5/2001 | Foley et al. | |
| 6,245,052 | B1 | 6/2001 | Orth et al. | |
| 6,280,399 | B1 | 8/2001 | Rossin et al. | |
| 6,283,948 | B1 * | 9/2001 | McKernan | A61B 17/3417 604/272 |
| 6,293,952 | B1 | 9/2001 | Brosens et al. | |
| 6,309,382 | B1 * | 10/2001 | Garrison | A61B 17/00234 604/26 |
| 6,331,180 | B1 | 12/2001 | Cosman et al. | |
| 6,374,135 | B1 | 4/2002 | Bucholz | |
| 6,416,520 | B1 | 7/2002 | Kynast et al. | |
| 6,551,240 | B2 * | 4/2003 | Henzler | A61B 1/0676 348/68 |
| 6,606,521 | B2 | 8/2003 | Paspa et al. | |
| 6,645,178 | B1 * | 11/2003 | Junker | A61M 25/0668 604/164.05 |
| 6,669,685 | B1 | 12/2003 | Rizoiu et al. | |
| 6,676,639 | B1 * | 1/2004 | Ternstrom | A61B 17/3417 604/174 |
| 6,685,630 | B2 * | 2/2004 | Sauer | A61B 17/34 600/104 |
| 6,761,725 | B1 * | 7/2004 | Grayzel | A61B 17/02 606/174 |
| 6,782,288 | B2 | 8/2004 | Truwit et al. | |
| 6,814,700 | B1 * | 11/2004 | Mueller | A61B 17/0293 600/201 |
| 6,942,634 | B2 | 9/2005 | Odland | |
| 6,989,003 | B2 | 1/2006 | Wing et al. | |
| 7,155,279 | B2 | 12/2006 | Whitehurst et al. | |
| 7,160,716 | B2 | 1/2007 | Kalina et al. | |
| 7,407,483 | B2 * | 8/2008 | Perez-Cruet | A61B 17/02 600/104 |
| 7,694,866 | B2 * | 4/2010 | Shifrin | A61B 17/115 227/179.1 |
| 7,744,596 | B2 * | 6/2010 | Young | A61B 18/1477 606/33 |
| 7,862,542 | B1 * | 1/2011 | Harmon, Sr. | A61B 1/00135 600/115 |
| 7,945,307 | B2 * | 5/2011 | Lubock | A61B 17/3468 128/899 |
| 8,192,445 | B2 * | 6/2012 | Parmer | A61B 19/201 600/426 |
| 8,323,185 | B2 | 12/2012 | Perez-Cruet et al. | |
| 8,992,558 | B2 * | 3/2015 | Stone | A61B 17/0218 600/204 |
| 2003/0045834 | A1 * | 3/2003 | Wing | A61B 17/34 604/161 |
| 2003/0073934 | A1 * | 4/2003 | Putz | A61M 25/0668 600/585 |
| 2003/0097149 | A1 * | 5/2003 | Edwards | A61B 17/00491 606/214 |
| 2003/0195392 | A1 | 10/2003 | Hamel et al. | |
| 2004/0024291 | A1 | 2/2004 | Zinkel | |
| 2004/0049208 | A1 * | 3/2004 | Hill | A61B 17/00008 606/145 |
| 2004/0059375 | A1 | 3/2004 | Ginn et al. | |
| 2004/0068172 | A1 | 4/2004 | Nowinski et al. | |
| 2004/0102804 | A1 * | 5/2004 | Chin | A61B 17/00008 606/190 |
| 2004/0176801 | A1 * | 9/2004 | Edwards | A61B 17/00491 606/214 |
| 2004/0186346 | A1 | 9/2004 | Smith et al. | |
| 2004/0215143 | A1 | 10/2004 | Brady et al. | |
| 2004/0217069 | A1 * | 11/2004 | Columbus | B01L 3/0293 210/782 |
| 2005/0065535 | A1 * | 3/2005 | Morris | A61B 17/0469 606/148 |
| 2005/0107820 | A1 * | 5/2005 | Forsberg | A61M 25/0606 606/194 |
| 2005/0143817 | A1 * | 6/2005 | Hunter | A61B 17/11 623/11.11 |

(56) References Cited

U.S. PATENT DOCUMENTS

| | | | |
|---|---|---|---|
| 2005/0159711 A1* | 7/2005 | Kathrani | A61B 17/34 604/264 |
| 2006/0276871 A1* | 12/2006 | Lamson | A61F 2/82 623/1.11 |
| 2006/0287583 A1 | 12/2006 | Mangiardi | |
| 2007/0021743 A1* | 1/2007 | Rioux | A61B 18/1477 606/32 |
| 2007/0100210 A1 | 5/2007 | Selover et al. | |
| 2007/0100211 A1 | 5/2007 | Selover et al. | |
| 2007/0260273 A1* | 11/2007 | Cropper | A61B 1/00087 606/185 |
| 2007/0270898 A1 | 11/2007 | Lillehei | |
| 2007/0276191 A1* | 11/2007 | Selover | A61B 1/06 600/245 |
| 2008/0109026 A1* | 5/2008 | Kassam | A61B 1/042 606/190 |
| 2008/0132933 A1* | 6/2008 | Gerber | A61B 17/3468 606/191 |
| 2008/0319268 A1* | 12/2008 | Michaeli | A61B 17/0218 600/202 |
| 2009/0048622 A1 | 2/2009 | Wilson | |
| 2009/0062618 A1* | 3/2009 | Drew | A61B 17/0218 600/204 |
| 2009/0137877 A1* | 5/2009 | Minnelli | A61B 17/0218 600/204 |
| 2009/0192444 A1* | 7/2009 | Albrecht | A61B 17/3474 604/26 |
| 2009/0259106 A1 | 10/2009 | Catapano et al. | |
| 2009/0312611 A1 | 12/2009 | Mangiardi | |
| 2009/0312783 A1* | 12/2009 | Whayne | A61B 17/320016 606/190 |
| 2010/0010315 A1 | 1/2010 | Mangiardi | |
| 2010/0312064 A1 | 12/2010 | Weisenburgh et al. | |
| 2010/0324488 A1* | 12/2010 | Smith | A61B 17/3417 604/164.11 |
| 2011/0046449 A1 | 2/2011 | Minnelli et al. | |
| 2011/0112360 A1* | 5/2011 | Swann | A61B 17/42 600/104 |
| 2011/0112375 A1 | 5/2011 | Bettuchi | |
| 2011/0144443 A1 | 6/2011 | Shelton et al. | |
| 2011/0196204 A1 | 8/2011 | Setty et al. | |
| 2011/0224742 A1 | 9/2011 | Weisel et al. | |
| 2011/0313286 A1* | 12/2011 | Whayne | A61B 18/148 600/431 |
| 2012/0010470 A1 | 1/2012 | Ducharme et al. | |
| 2012/0071748 A1* | 3/2012 | Mark | A61B 17/320016 600/411 |
| 2012/0109279 A1* | 5/2012 | Mayberry | A61F 2/07 623/1.11 |
| 2012/0123327 A1* | 5/2012 | Miller | A61M 25/0012 604/95.04 |
| 2012/0165611 A1 | 6/2012 | Warren et al. | |
| 2013/0102851 A1 | 4/2013 | Mark et al. | |
| 2013/0204287 A1 | 8/2013 | Mark et al. | |
| 2013/0211202 A1 | 8/2013 | Perez-Cruet et al. | |
| 2013/0281791 A1 | 10/2013 | Aferzon | |
| 2014/0042083 A1* | 2/2014 | Mallard | B01D 36/045 210/512.1 |
| 2014/0142394 A1 | 5/2014 | Cataltepe | |
| 2014/0142420 A1* | 5/2014 | Jackson, III | A61B 1/00135 600/424 |
| 2014/0171873 A1 | 6/2014 | Mark | |
| 2014/0187922 A1 | 7/2014 | Mark et al. | |
| 2014/0249371 A1* | 9/2014 | Fischvogt | A61B 17/3417 600/114 |
| 2015/0032022 A1 | 1/2015 | Stone et al. | |
| 2015/0313631 A1* | 11/2015 | Fischvogt | A61B 1/313 264/255 |

FOREIGN PATENT DOCUMENTS

| | | | |
|---|---|---|---|
| WO | WO-2006017507 A2 | 2/2006 | |
| WO | WO-2006050047 A2 | 5/2006 | |
| WO | WO-2007002251 A2 | 1/2007 | |
| WO | WO-2008066543 A1 | 6/2008 | |
| WO | 2008121294 A1 | 10/2008 | |
| WO | 2009103759 A1 | 8/2009 | |

OTHER PUBLICATIONS

PCT International Search Report & Opinion dated Apr. 9, 2013 for PCT/US2012/061568.

Office Action dated May 9, 2013 for U.S. Appl. No. 11/665,666.

A. Schupak, "A Healthy Glow Florescent imaging helps surgeons cut more cancer cells," Poplar Science, Feb. 2011.

Modern Medicine, "New Device May Help Surgeons Resect Brain Tumors," "Fluorescence spectroscopy helps neurosurgeons identify hard-to-see tumor tissue," (Jan. 31, 2011).

Nader Sanal, MD, et al., "Intraoperative Confocal Microscopy for Brain Tumors: A Feasibility Analysis in Humans," www.neurosurgery-online.com (Jun. 2011).

Juan C. Fernandez-Miranda, M.D., et al. "High-definition fiber tracking guidance for intraparenchmyal endoscopic port surgery," J. Neurosurg/vol. 113/Nov. 2010.

Manuel Dujovny, et al., "Brain Retractor Systems," Neurological Research, vol. 37, No. 7, (2010).

T. Nakano, et al., "Endoscopic Treatment for Deep-seated or Multiple Intraparenchymal Tumoers: Technical Note," Dept. Of Neurosurgery, Hirosaki University Graduate School of Medicine. (2009).

Amin b. Kassam, et al., "Completely endoscopic resection of intraparenchymal brain tumors," Neurosurg./ vol. 110/ Jan. 2009.

K. Ogura, et al., "Neurosurgical Technique, New microsurgical technique for intraparenchymal lesions of the brain: transcylinder approach," Acta Neurochir (Wien)(2006).

Chun-Chung Chen, M.D., et al., "A stainless steel sheath for endoscopic surgery and its application in surgical evacuation of putaminal haemorrhage," Journal of Clinical Neuroscience (2005).

O. Barlas, et al., Clinical Article, "Stereotactically guided microsurgical removal of colloid cysts," Acta Neurochir (Wien)(2004).

Tetsuhiro Nishihara, M.D., et al., "A transparent sheath for endoscopic surgery and its application in surgical evacuation of spontaneous intracerebral hematomas," J. Neurosurg/vol. 92/Jun. 2000.

Donald M. O'Rourke, M.D., et al., "Vycor Medical, Inc.—Business Summary," www.vycormedical.com.

Non-Final Office Action dated Nov. 10, 2011 for U.S. Appl. No. 11/665,666.

PCT International Search Report dated Jun. 20, 2006 for PCT/US05/39185.

Wedeen, Van J., et al., "The Geometric Structure of the Brain Fiber Pathways," Science 335, 1628 (2012).

Response to Non-Final Office Action dated Nov. 10, 2011 for U.S. Appl. No. 11/665,666.

Final Office Action dated May 30, 2012 for U.S. Appl. No. 11/665,666.

Response to Final Office Action dated May 30, 2012 for U.S. Appl. No. 11/665,666.

PCT International Search Report and Written Opinion dated Sep. 21, 2015 for PCT/US2015/018573.

\* cited by examiner

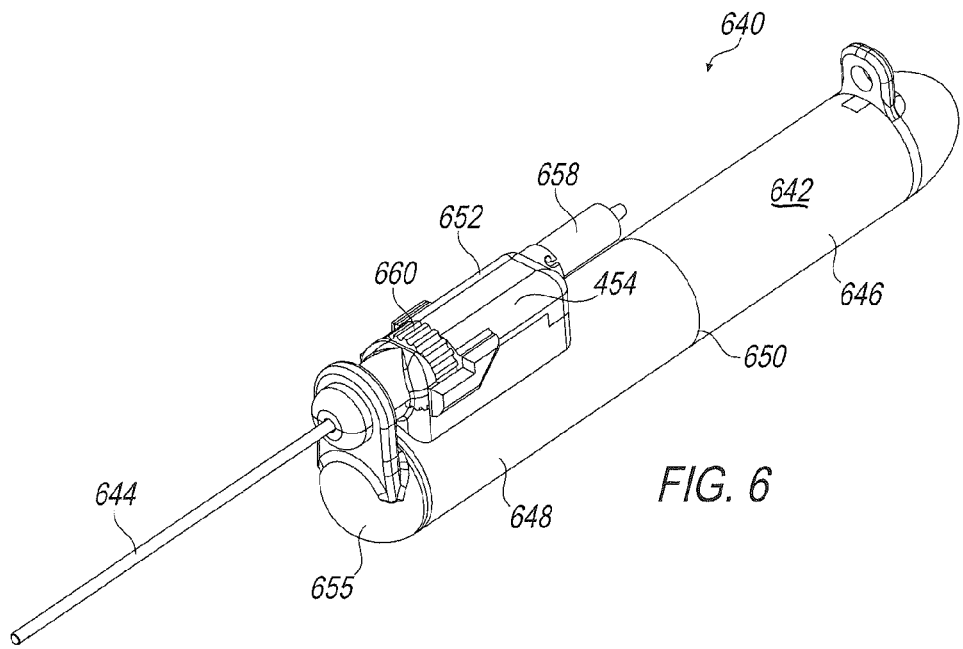
FIG. 6
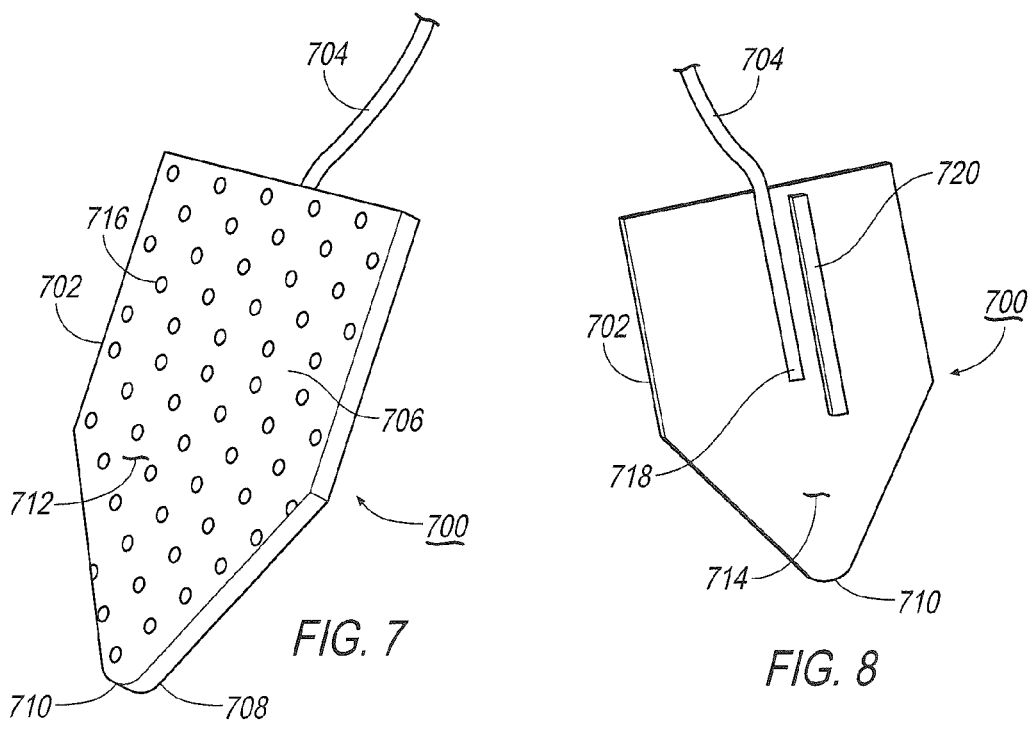
FIG. 7
FIG. 8

SURGICAL ACCESS ASSEMBLY AND METHOD OF USING SAME

CROSS-REFERENCE TO RELATED APPLICATIONS

This application is a continuation-in-part application of co-pending U.S. patent application Ser. No. 13/280,015, filed on Oct. 24, 2011, the contents of which are incorporated by reference in its entirety.

TECHNICAL FIELD

The present disclosure relates generally to a surgical system for use with delicate and critical tissues, as well as methods of accessing and performing surgery using same.

BACKGROUND

Diagnosis and treatment of conditions affecting the brain are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, glioblastomas (GB) and metastases (mets) manifest themselves in the intraparenchymal subcortical space (i.e., the white matter) of the brain are particularly challenging to access, let alone treat. The ventricles of the brain contain eloquent communication structures (neural network) which are located in the subcortical space, called fiber tracts and fascicles. Thus, traditionally, unless the ICH, GB, and/or mets where considered anything but "superficial," such conditions have been considered inoperable, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI), Diffusion Tensor Imaging (DTI) and Navigation systems (instrument position tracking systems). These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including fiber tracts and fascicles. If an abnormality is identified through the use of one or more imaging modalities and/or techniques, it may be necessary or desirable to biopsy or remove the abnormality.

Once a course of action has been determined based upon one or more imaging techniques, a surgical treatment may be necessary or desired. In order to operate surgically on the brain, access must be obtained through the skull and delicate brain tissue containing blood vessels and nerves that can be adversely affected by even slight disturbances. Therefore, great care must be taken in operating on the brain so as not to disturb delicate blood vessels and nerves to prevent adverse consequences resulting from a surgical intervention.

Traditionally, accessing abnormalities which manifest in deeper spaces within the brain has meant a need for a surgery that creates a highly invasive approach. In some instances, in order to obtain access to target tissue, a substantial portion of the skull is removed and entire sections of the brain are retracted to obtain access. For example, surgical brain retractors are used to pull apart or spread delicate brain tissue, which can leave pressure marks from lateral edges of the retractor. In some instances, a complication known as "retraction injury" may occur due to use of brain retractors. Of course, such techniques are not appropriate for all situations, and not all patients are able to tolerate and recover from such invasive techniques.

It is also known to access certain portions of the brain by creating a burr hole craniotomy, but only limited surgical techniques may be performed through such smaller openings. In addition, some techniques have been developed to enter through the nasal passages, opening an access hole through the occipital bone to remove tumors located, for example, in the area of the pituitary.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance, in which an image of the surgical instrument is superimposed on a pre-operative image to demonstrate the location of the instrument to the surgeon and trajectory of further movement of the probe or instrument.

In recent years, there has been a focus on developing surgical access systems to provide access to previously difficult to access areas. However, while access systems proposed so far may provide a manner to access certain brain tissue, such systems are configured with a blunt shaped distal end, which can actually cause transient or even permanent deformation and trauma of delicate tissue structures which can manifest itself in temporary or permanent neurological deficits after surgical cytoreduction due to damage of blood vessels, cranial nerves, fiber tracts and fascicles.

During a procedure, it is often necessary to protect certain critical vessels and/or structures that are adjacent an area to be operated on in the surgical field. It is known to use surgical patties to cover such vessels or structure. However, there are certain issues with known surgical patties.

First, known surgical patties are constructed of absorbent cotton gauze, which may be chemically bonded to one another to give the gauze a relative high wet strength. The resulting gauze structure has a surface that contains various absorbent fibers. As the surgical patty is left in place in the surgical field, the fibers become permeated by the fluid present and may tend to adhere to the body tissue to which the gauze structure comes into contact. Thus when the surgical patties are placed upon the tissue and moved along or removed from the surgical field, such movement can actually abrade and tear tissue, causing damage to the delicate neurovascular tissues that the patties are being used to protect from other instrumentation used during the procedure.

Another issue experienced with known surgical patties is the challenge of maintaining the position and location of the of the patty retrieval string during the surgical procedure to prevent them from falling into the surgical field during a surgical procedure. Known systems use locking surgical clamps called "snaps" or other similar devices to hold the position of the surgical patty string within the surgical field. When it comes to repositioning or removal of the patty within the surgical field, these holding devices must again be removed from the patty string to reposition the pattie and then re-applied.

Notwithstanding the foregoing advances, there remains a need for improved surgical techniques and apparatuses for operating on brain tissue. There also exists a need for improved surgical patties to address the specific challenges of minimally invasive neurosurgery, which includes the management of retaining and retracting of the strings for such patties.

BRIEF DESCRIPTION OF THE DRAWINGS

Exemplary embodiments of the present disclosure will now be described in greater detail with reference to the attached figures, in which:

FIG. 6 is a perspective view of an exemplary surgical device used for cytoreduction.

FIG. 7 is a perspective view of a first side of an exemplary surgical-patty.

FIG. 8 is a perspective view of a rear side of the surgical-patty of FIG. 5.

DETAILED DESCRIPTION

Figure 1:
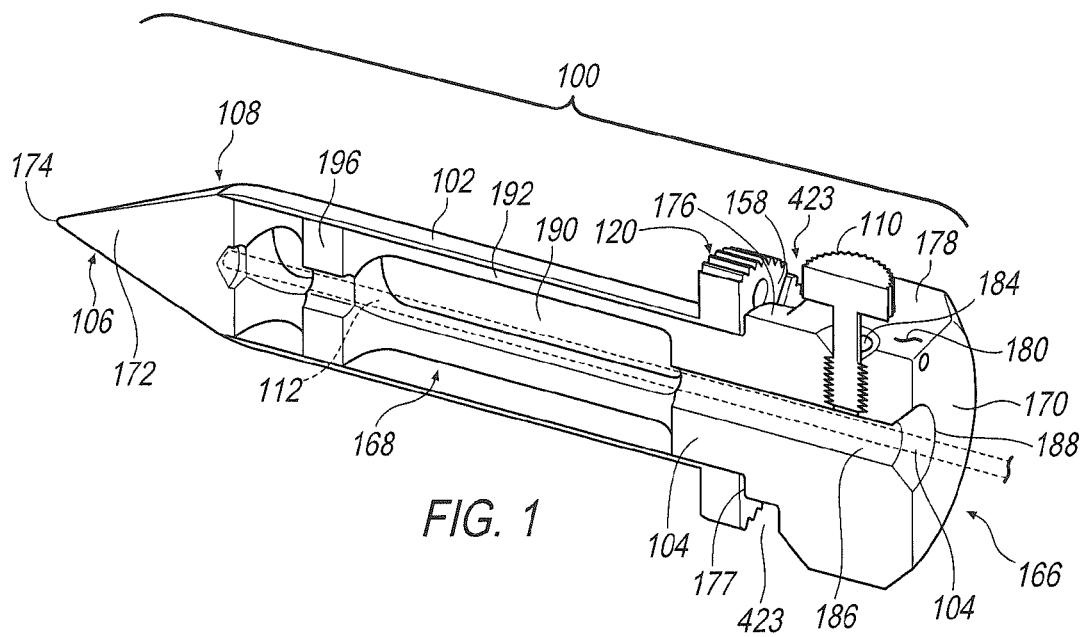
FIG. 1 is a perspective cross-sectional view of an exemplary arrangement of a surgical access assembly.

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly, various components for use in same, and a method of using the surgical access assembly. The components disclosed herein provide surgeons with an enhanced ability to minimize trauma to the patient, while providing efficient improved minimally invasive surgical techniques, such as, for example, during intracranial surgical techniques.

Referring to FIG. 1, a perspective cross-sectional view of a surgical access assembly 100 is shown. In one exemplary arrangement, surgical access assembly 100 comprises a hollow outer sheath 102 and a selectively removable obturator 104. Obturator 104 is configured with a length that is longer than a length of outer sheath 102 such that a distal end 106 of obturator 104 protrudes a predetermined distance from a distal end 108 outer sheath 102, as will be discussed below in greater detail.

A locking member 110 may also be provided. Locking member 100 is configured to operatively retain a separate navigation member 112 (shown in phantom) within obturator 104, as will be discussed in greater detail below. A retaining member 114 may be secured within a portion of obturator 104 to prevent locking member 110 from being completely disengaged from obturator 104.

Figure 2:
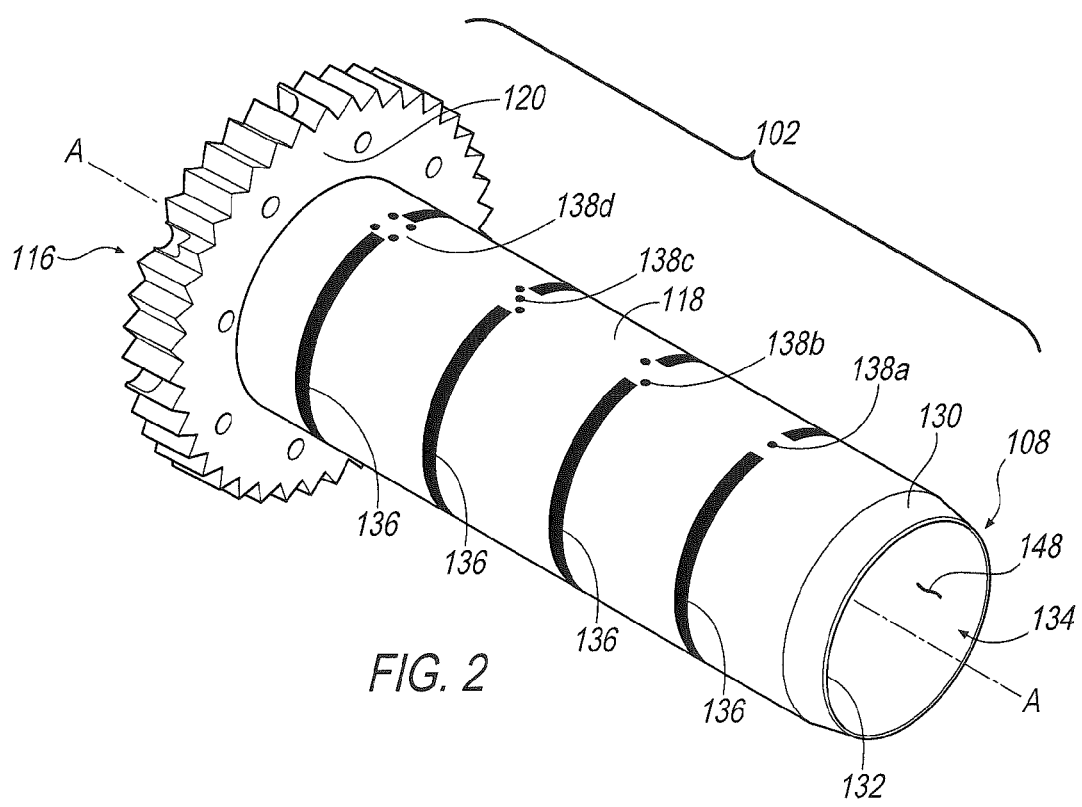
FIG. 2 is a perspective view of an outer sheath of the surgical access assembly of FIG. 1.

Referring now to FIG. 2, outer sheath 102 will be described in greater detail. Outer sheath 102 is defined by distal end 108 and a proximal end 116 and includes a generally hollow body portion 118 and a grip portion 120. In one exemplary arrangement, grip portion 120 is configured as a ring, as illustrated in the drawings. However, it is understood that grip portion 120 need not be configured as a ring. For ease of explanation, grip portion 120 will be referred to hereinafter as grip ring 120. Grip ring 120 is fixedly secured to body portion 118 at proximal end 116. In one exemplary arrangement, body portion 118 is constructed of a clear biocompatible material that permits viewing of normal tissue, abnormal tissue, as well as critical structures that are disposed outside of body portion 118 when outer sheath 102 is disposed within such tissue. In one exemplary arrangement, outer sheath 102 is constructed of polycarbonate, though other biocompatible materials may be employed, including resins.

In one exemplary configuration, an imaging mechanism may be incorporated into outer sheath 102 that would permit visualization of tumors, vessels, fiber tracks, fascicles and even healthy tissue, in real-time. Indeed, as will be explained in further detail below, the imaging mechanism will enable physiological functional imaging to provide information about the characteristics of the cortical fiber tracks to be visible, be visible, thereby enabling a user to separate and park such fibers on either side of outer sheath 102 rather than cutting, stretching and potentially damaging such fibers while gaining access to a desired location within the brain. Further, as will be explained in further detail below, the imaging mechanism may also enable the surgeon to have real-time information about the fiber tract and fascicle location, after placement of outer sheath 104, and during abnormality resection procedure therethrough. In addition to white matter tract imaging, mapping of the characteristics of the cerebral blood flow may be obtained.

In one exemplary embodiment, the imaging mechanism may be an ultrasound probe incorporated into outer sheath 102. For example, outer sheath 102 may be provided with one or more channels within the wall that defines outer sheath 102 that are configured with one or more small diameter ultrasound probes. In another arrangement, a single ultrasound probe that is configured to be received within outer sheath 102 may be provided. In yet another embodiment, a low field MRI probe may be selectively placed in outer sheath 102 to provide enhanced imaging. In yet another embodiment a low field MRI imaging coil may be molded into or bonded into outer sheath 102. In still another exemplary arrangement, the probe may be an optical coherent tomography (OCT) imaging or spectroscopy.

Distal end 108 of outer sheath 102 may be configured with a tapered portion 130 that extends towards a center axis A-A of outer sheath 102 to a distal edge 132 that surrounds an opening 134 in distal end 108 of outer sheath 102. Tapered portion 130 serves to ease the transition between outer sheath 102 and a distal tip potion 172, without drag, trauma or coring of tissue from a diameter that defines a body portion of obturator 104 to a diameter that defines body portion 118 of outer sheath 102. In one exemplary configuration, distal end 108 may be configured with a radius or other configuration so as to create a smooth/atraumatic transition of the brain tissue when surgical access assembly 100 is inserted into the brain.

For example, distal edge 132 is configured so as to be non-sharpened and radiused. In one exemplary arrangement, distal edge 132 is configured as a 0.3 mm diameter radiused rim. Tapered portion 130 and radiused distal tip 132 cooperate with obturator 104 to atraumatically move tissue, as well as various structures within the brain, including white matter, away from outer sheath 102 without cutting tissue or such structures. Indeed, unlike prior art devices that include either a blunt tip distal end or a tapered leading edge, radiused distal tip 132 cooperates with tapered portion 130 and obturator 104 to prevent bruising and damage to various tissue. More specifically, this configuration facilitates entry of outer sheath 102 into delicate tissue, but without cutting such delicate tissue. Insertion of surgical access assembly 100 will be explained in further detail below.

Body portion 118 may further be provided with a plurality of spaced apart indicators 136. Indicators 136 generally extend about the circumference of body portion 118 and each may further incorporate a secondary indicator 138 that visually illustrates a predetermined location on body portion 118, as shown in FIG. 2. While FIG. 2 illustrates four indicators 136, it is understood that body portion 118 may be provided in a variety of lengths and that any number of indicators 136 may be provided. Body portion 118 may also be provided with a longitudinal indicator (not shown). An exemplary longitudinal indicator 140 is described in co-pending U.S. patent application Ser. No. 13/280,015, the contents of which are incorporated in its entirety. Indicators 136 and 138 may be printed onto either an internal or external surface of body portion 118 with an imaging visible ink such as, for example ink containing fluro-deoxyglucose (FDG), Technicium 99, Gadolinium, titanium dust, barium sulfate, a combination of the above or other suitable imaging material. Indicators 136 and 138 provide a reference point for the operator of system 100, as structures may be visible through body portion 118. Indicator 136, and 138 may also be configured to be visible under MRI, CT, PET, or any other suitable imaging modality to enable easy identification of areas of interest. In one alternative embodiment, indicators 136, and 138 may be etched or printed onto body portion 118, either on the internal or external surface of body portion 118.

Figure 3:
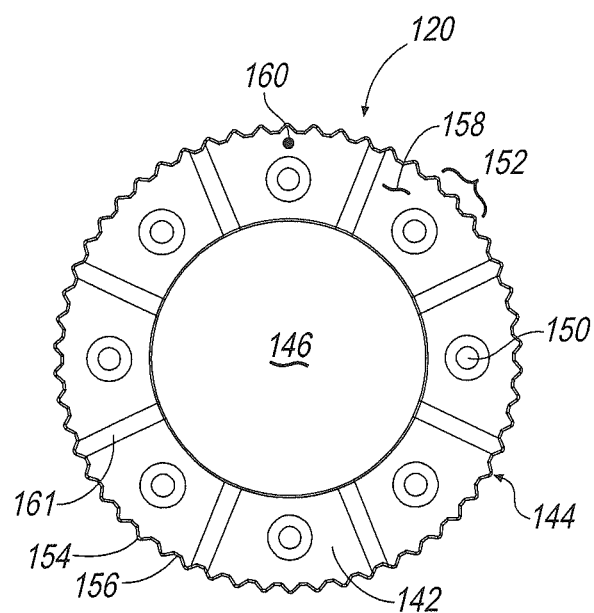
FIG. 3 is an end view of the outer sheath of FIG. 2.

Details of grip ring 120 are best seen in FIG. 3. Grip ring 120 is generally configured as a flange member 142 defined by an outer periphery 144 and an inner opening 146. Inner opening 146 may be sized to generally correspond to the diameter of a lumen 148 defined by body portion 118. Outer periphery 144 is sized to have a diameter that is larger than lumen 148 of body portion 26. Flange member 142 may further be provided with one or more small openings 150 that are disposed therein. In one exemplary arrangement, a plurality of small openings 150 are provided that are spaced generally equi-distantly about inner opening 146. Small openings 150 will be described in further detail below. Outer periphery 144 may further be provided with a textured surface 152 to provide for ease of gripping outer sheath 102. For example, in one exemplary arrangement, textured surface 152 comprises a plurality of alternating ridges 154 and grooves 156. However, it is understood that other textured surfaces may be employed.

Disposed on a proximal end surface 158 of flange member 142, an alignment feature 160 may be provided. Alignment feature 160 may be used to indicate the location of longitudinal indicator 140 when outer sheath 102 is positioned within the brain.

In one exemplary configuration, end surface 158 may be provided with at least one retaining notch 161. Retaining notch 161 extends from outer periphery 144 to a periphery of inner opening 146. As will be explained in further detail below, retaining notch 161 is configured to retain a string or cord from a surgical-patty, other absorbent surgical sponge or other object to be temporarily positioned within outer sheath 102.

Figure 4:
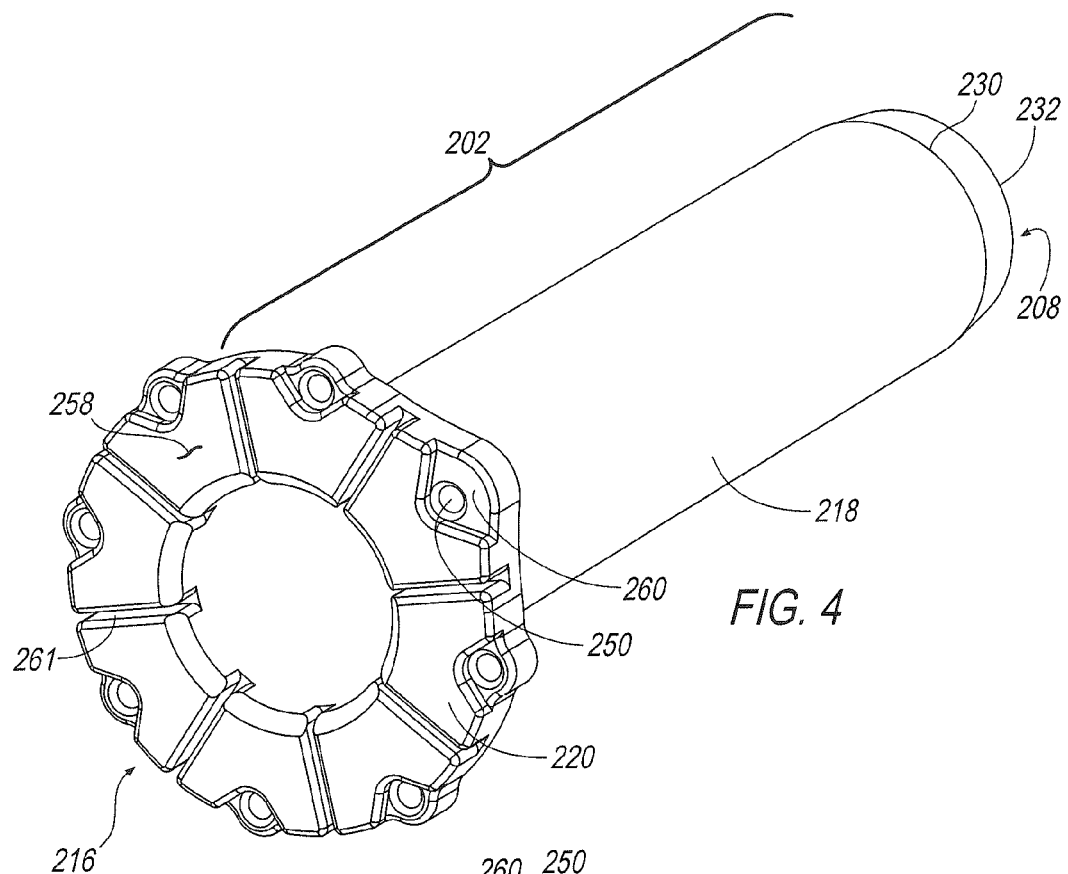
FIG. 4 is a perspective view of an alternative arrangement of an outer sheath of a surgical access assembly.
Figure 5:
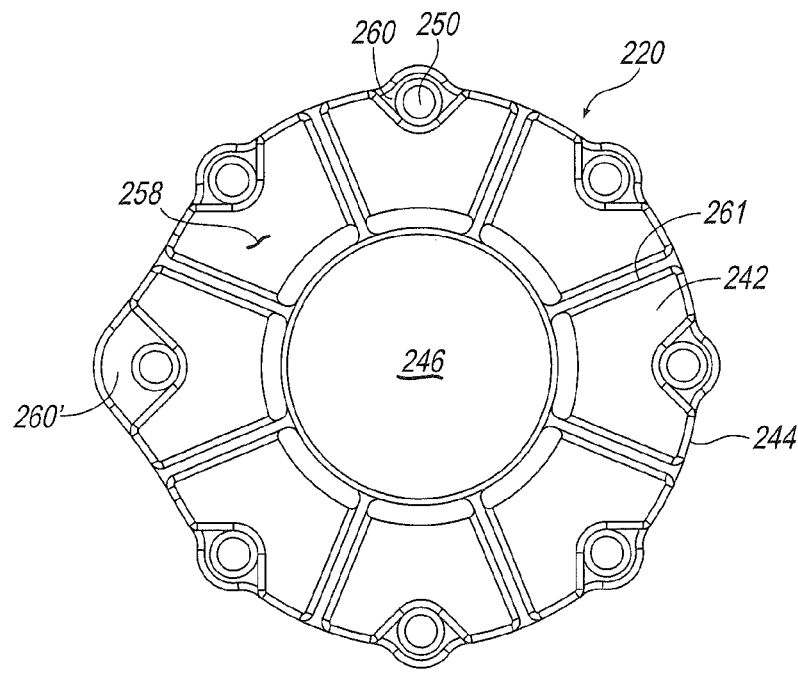
FIG. 5 is an end view of the outer sheath of FIG. 4.

An alternative arrangement of an outer sheath 202 is illustrated in FIGS. 4-5. Outer sheath 200 is similar to outer sheath 102. Outer sheath 202 is defined by a distal end 208 and a proximal end 216 and includes a generally hollow body portion 218 and a grip portion 220. Grip portion 220 is fixedly secured to body portion 218 at proximal end 216. In one exemplary configuration body portion 218 is construction of a clear biocompatible material that permits viewing of tissue, as well as critical structures that are disposed outside of body portion 218 when outer sheath 202 is disposed within tissue. In one exemplary configuration, outer sheath 202 is constructed of polycarbonate, though other biocompatible materials may be employed, including resins. Similar to outer sheath 102, outer sheath 202 may also incorporate an imaging mechanism, as described above.

Distal end 208 of outer sheath 202 may also be configured with a tapered portion 230 that extends towards a center axis of outer sheath 202 to a distal edge 232 that surrounds an opening in distal end 208 of outer sheath 202. Distal end 208 may be configured with a radius or other configuration so as to create a smooth/atraumatic transition of brain tissue when surgical access assembly 200 is inserted into the brain.

While not shown, body portion 218 may further be provided with a plurality of spaced apart indicators, similar to that shown with respect to body portion 118.

Details of grip portion 220 are best seen in FIG. 5. Grip portion 220 is generally configured as a flange member 242 defined by an outer periphery 244 and an inner opening 246. Inner opening 246 may be sized to generally correspond to the diameter of a lumen defined by body portion 218. Outer periphery 244 is sized to have a diameter that is larger than lumen 248 of body portion 218.

Flange member 242 may further be provided with one or more small openings 250 disposed therein. Unlike flange member 142 of outer sheath 102, in the exemplary configuration, openings 250 are positioned adjacent outer periphery 244 such that opening 250 are positioned outboard from the lumen of outer sheath 202, as will be explained in further detail below.

In one exemplary configuration, portions 260 surrounding small openings 250 may be axially offset from a proximal end surface 258 of flange member 220. More specifically, portions 260 of flange member 220 may be configured with a thickness that is less than the remainder of flange member 220. Portions 260 may extend slightly radially outward from outer periphery 244. One of portions 260' may extend further radially outward than the remainder of portions 260 so as to serve as an alignment feature. The alignment feature 260' may be used to indicate the location of the longitudinal indicator disposed on outer sheath 202 when outer sheath 202 is positioned within the brain.

The alignment feature may also be used for the alignment, attachment or coupling to other devices, such as but not limited to imaging devices. Similarly, openings 250 may be used in a similar fashion. Feature 260 may also be aligned and used to indicate the location of an area of surgical interest within the tissue or in conjunction with the depth indicators 136 illustrated in FIG. 2 for the same purposes. Because outer sheath is fabricated of a CT, MRI and PET safe and image compatible material, outer sheath 102/202 is especially useful for use with intraoperative surgical imaging and application platforms.

In one exemplary configuration, end surface 258 may also be provided one or more retaining notches 261. Each retaining notch 261 is configured to extend from outer periphery 244 to a periphery of inner opening 246. In one exemplary configuration (as best seen in FIG. 4), retaining notches 261 do not extend through the thickness of the flange member 220, including at the outer periphery 244. As will be explained in further detail below, retaining notches 261 are configured to retain a string or cord from a surgical patty, other absorbent surgical sponge or other object to be temporarily positioned within outer sheath 102.

Obturator 104 may be seen in FIG. 1. Obturator 104 is defined by distal end 106, a proximal end 166, a body portion 168 and a handle portion 170. Distal end 106 is configured with a generally conical shaped distal tip portion 172 that tapers to a tip member 174 to provide atraumatic dilation of tissue. In one exemplary arrangement, tip portion 172 tapers toward a closed tip member 174 so as to prevent coring of tissue as obturator 104 is inserted into the brain. Further details of an exemplary obturator may be found in co-pending U.S. patent application Ser. No. 13/280,015.

Distal tip 174 is configured to be radiused such that tip member 174 is rounded, and neither blunt, nor sharp. More specifically, tip member 174 is configured so as not to have any flat portions which during insertion can stretch or even tear the delicate tissues such as the vessels, fiber tracts and fascicles found in the brain. Further, because tip member 174 is closed, damage of such delicate tissues and fascicles are also avoided. In one exemplary embodiment, tip member 174 is configured with a 0.5 mm radius. As will be explained in further detail below, the configuration of tip member 174 is designed to gently displace and move the tissue into which it is inserted; i.e., atraumatically dilate the tissue to allow for introduction in to an intra-fascilar and para-fascilar manner, as opposed to cutting tissue as surgical access assembly 100 is inserted into the tissue.

Handle portion 170 is positioned at proximal end 166 of obturator 104. Handle portion 170 comprises a stop member 176 and a grip member 178. Stop member 176 is positioned distally of grip member 178 and is configured to have a width that is greater than a diameter of body portion 168, as well as a diameter of outer sheath 102. Grip member 178 is configured with a width W2 that is greater than the width W1 of stop member 176, thereby providing a step-like configuration. Stop member 176 may further define an engagement surface 177 that is axially spaced from a distal surface of grip member 178.

In one exemplary arrangement, handle portion 170 is configured with a generally planar surface 180. Planar surface 180 may be configured with a receiving aperture 184 that is configured to receive locking member 110. In one exemplary arrangement, receiving aperture 184 is threaded. Disposed within receiving aperture is in communication with a channel 186 that extends at least partially thorough handle portion 170. After locking member 110 is at least partially engaged within receiving aperture 184, a retaining member (not shown) may be positioned within channel 186.

An access opening 188 is formed through proximal end 166. Access opening 188 extends through handle portion 170.

In one exemplary arrangement, access opening 188 may be provided with an inwardly extending chamfer that tapers toward access opening 188. The chamfer may provide a self-directing feature for inserting a navigation member (shown in phantom) into access opening 188. Access opening 188 is in communication with a first channel segment that extends through handle portion 170 and into body portion 168.

Body portion 168 extends between distal end 106 and proximal end 166. Body portion 168 may include one or more elongated void areas 190. Void areas 190 serve to reduce weight of obturator 104, thereby making obturator 104 easier to manipulate during surgical procedures. Void areas 190 also facilitate sterilization of obturator 104 by moisture retention within body portion 168 of obturator 104. Further, void areas 190 also provide venting, thereby preventing a vacuum from being generated as obturator 104 is being withdrawn from outer sheath 102 during operation. Void areas 190 are separated by web portions 192 that extend axially through a portion of the length of body portion 168.

Body portion 168 may further include one or more cross webs 196. Cross webs 196 are oriented transverse to web portions 192 and connect web portions 192 together. In one exemplary arrangement, body portion 168 includes at least one cross web 196 that operatively defines the outer diameter of body portion 168. The outer diameter is sized to fit within a lumen of outer sheath 102 such that obturator 104 and outer sheath 102 may be selectively slid relative to one another. However, the outer diameter is also sized to minimize or even eliminate any gaps between an inner surface of outer sheath 102 and an outer surface of obturator 104. Cross webs 196 serve to provide for structural integrity of obturator 104, as well as improved rigidity.

Use of surgical access assembly 100 will now be described in the context of a surgical procedure. In operation, once a plan for a surgical trajectory is developed, the surgeon creates the craniotomy and Dural access incision. Next, the obturator 104 is inserted into outer sheath 102 until grip ring 120 abuts first stop member 176, as shown in, for example FIG. 1. Navigation member 112 may then be operatively connected to obturator 104. As discussed in co-pending U.S. patent application Ser. No. 13/280,015, various types of navigation members may be used and the disclosure is not limited to the arrangement disclosed herein.

Once surgical access assembly 100 is assembled and operatively connected to a navigational system, surgical access assembly 100 is navigated to area of interest. In one exemplary arrangement, distal tip 178 of obturator 104 is directed to a furthermost outer margin of an area of interest, as discussed in co-pending U.S. patent application Ser. No. 13/280,015.

Due to the tapered configuration and closed, radiused distal tip 174 of obturator 104, as well as the radiused distal tip 132 of outer sheath 102, as surgical access assembly 100 is inserted into the brain and navigated to the area of interest, tissue is gently pushed to either side of surgical access assembly 100, so as to atraumatically dilate tissue, while minimizing trauma to the tissue. Further, because surgical access assembly 100 is operatively connected to navigation member 112, as surgical access assembly 100 is being inserted into the brain tissue, navigation member 112 may cooperate with an imaging modality to providing real-time information concerning fiber tact in trajectory T, thereby allowing the surgeon to minimize fiber tract compromise or damage during insertion of surgical access assembly 100.

Once surgical access assembly 100 is positioned at the area of interest, navigation member 112 removed from or detached from surgical access assembly 100.

Outer sheath 102 is then operatively positioned with respect to the area of interest 500. More specifically, outer sheath 102 is decanted with respect to obturator 104 such that distal end 108 of outer sheath 102 is moved toward distal end 106 of obturator 104, as discussed in co-pending U.S. patent application Ser. No. 13/280,015. This action is accomplished by grasping grip ring 120 with one hand while maintaining obturator 104 stationary, such, for example, grasping grip member 178 with another hand. Grip ring 120 may be gently rotated and/or swiveled with respect to a central axis of obturator 104 to enable outer sheath 102 to be moved distally with respect to obturator 104. First stop member 176 aids in gripping and manipulating outer sheath 102, in that a gap 423 (see FIG. 1) is created between an end surface of the grip ring 120 and a distal end surface of grip member. Outer sheath 102 is decanted a distance that generally corresponds to the length of distal tip portion 172 of obturator 104, thereby positioning outer sheath 102 within the area of interest 500.

Once outer sheath 102 is appropriately positioned, obturator 104 is then removed from outer sheath 102. More specifically, outer sheath 102 is maintained to be relatively stationary at the area of interest 500, and obturator 104 is moved in a proximal direction until fully removed from outer sheath 102. This action results in outer sheath 102 forming a pathway to the area of interest 500.

Outer sheath 102 may then be secured in place so as to prevent cranial pressure from pushing outer sheath 102 out of the brain tissue. In one exemplary arrangement, a securing member may be utilized with small openings 150 on grip ring 120 (or opening 250 on grip member 220) to temporarily secure outer sheath 102. However, the securing member may be secured so as to permit a limited degree of movement so as to result in a floating system that permits selective repositioning. Suitable securing members include, but are not limited to, bridle sutures, flexible bands with retaining hooks, or even repositionable retractor arms.

Once outer sheath 102 is properly positioned, debulking area of interest 500 may be conducted. Traditionally, a patient is given medication, such as, for example, Mannitol, before an intracranial operation to reduce intracranial pressure (ICP) of the brain prior to the surgery. Indeed, ICP is often experienced by patients due to the natural response of the craniotiomy and/or the present of an abnormality within the brain. The present inventors have found that it may be advantageous to omit or minimize the use of medication for reducing ICP. More specifically, by not reducing ICP, because the brain tends to occupy the available space within the skull, after obturator 104 is removed from outer sheath 102, the target tissue may have a tendency to flow into, and present itself into the open distal end 108 of outer sheath 102, due to the cranial pressure. The area of interest 500 may actually move into outer sheath 102 on its own, thereby assisting in the delivery and minimizing manipulation required of outer sheath 102 during the process.

It is contemplated that a wide range of surgical devices may be inserted into outer sheath 102 to remove tissue abnormalities. In one exemplary arrangement, it is contemplated that outer sheath 102 may have an inner diameter up to approximately 20 mm, to allow multiple instruments, such as graspers, dissectors, scissors, cautery and suction instruments to be inserted through outer sheath 102 to perform surgery.

One exemplary surgical device that may be used is the NICO MYRIAD® manufactured and distributed by Nico Corporation of Indianapolis, Ind. Referring to FIG. 4, an exemplary surgical cutting device 640 is shown, such as that disclosed in co-pending, and co-owned with the assignee of the present application, U.S. patent application Ser. No. 12/389,447, the contents of which are incorporated by reference in its entirety. Surgical cutting device 640 includes a handpiece 642 and a cutting element that includes an outer cannula 644 and an inner cannula (not shown). In one exemplary configuration, handpiece 642 is configured with a generally cylindrical shape. Handpiece 642 may be sized and shaped to be grasped with a single hand Handpiece 642 also includes a lower housing 650 comprising a proximal section 646 and a distal section 648. A front housing section 655 may be connected to a cam housing positioned in distal section 648. An upper housing 652 is also provided. The cutting element is mounted to upper housing 652 and may be fluidly connected to a tissue collector 658. In one exemplary arrangement, tissue collector 658 may be operatively connected directly to upper housing 652. Alternatively, tissue collector 658 may be remotely connected to the cutting element by appropriate tubing. A vacuum line (not shown) may be connected to a proximal end of tissue collector 658 to direct tissue into the cutting element, as well as to deliver severed tissue to tissue collector 658. A rotation dial 660 for selectively rotating the outer cannula 644 with respect to handpiece 642 is also mounted to upper housing 652, to provide controlled cutting action.

Use of surgical device 640 is advantageous in that space is limited to effectuate tissue debulking, such that use of traditional surgical scissors may be challenging, especially when other instruments are inserted into outer sheath 102 simultaneously. Moreover, fibrosity of a tumor may present challenges for the use traditional suction debulking devices. Traditional graspers operate by tearing tissue of interest. However, the tearing action may become problematic if vessels or fascicles are too close to the tissue being torn in that such vessels or fascicles may also be torn.

As the area of interest 500 is cytoreductively debulked, it may become necessary to reposition or move outer sheath 102. If repositioning is necessary, in one exemplary arrangement, manipulation members may be provided. Examples of manipulation members are discussed in co-pending U.S. patent application Ser. No. 13/280,015.

Outer sheath 102 is configured such that multiple instruments may be inserted simultaneously therewithin, thereby increasing the speed and safety of surgical procedures. In one exemplary arrangement, an endoscope may be partially inserted and held to one side of outer sheath 102, to provide an image of area of interest 500 to a monitor, while a surgical instrument, such as surgical instrument 640 is also inserted within outer sheath 102. An illuminating ring may also be used, (as described in co-pending U.S. patent application Ser. No. 13/280,015, for example) with the endoscope and the surgical instrument being inserted through an access opening that aligns with opening 146 of grip ring 120. Because the illuminating ring provides light for outer sheath 102, a relatively small diameter endoscope may be use, thereby increasing the available space within outer sheath 102 for other surgical instruments. In another exemplary configuration, the surgeon may have both a surgical instrument and a cautery instrument simultaneously inserted into outer sheath 102, thereby permitting the surgeon to cauterized vessels that are encountered during the procedure.

Because outer sheath 102 may be directly positioned at the area of interest in such a manner as to avoid unnecessary damage to critical structures, and because surgical device 640 may be placed directly at the sight of area of interest, utilizing surgical access system 100 provides the ability to resect most of an area of interest, such a tumor. As one of ordinary skill in the art can appreciate, the more that a tumor is resected and removed, the less therapy is required for treatment. In other words, the more diseased tissue there is resected, the less diseased tissue there is to destroy.

During a surgical procedure, oftentimes the surgeon deploys surgical patties or pledgets at or adjacent the area of interest. Surgical patties are utilized in brain in spinal surgery procedures for a variety of functions. One such function is to protect brain and neural tissue from instrumentation being deployed adjacent to such brain and neural tissue. Another function is to permit removal of fluids that might interfere with or obscure the surgical procedures and treatments being performed at the area of interest.

However, certain problems exist with current surgical patties. Certain known surgical patties are constructed of absorbent cotton gauze, which are chemically bonded to one another to give the felt a relative high wet strength. Thus, the resulting gauze structure has a surface that contains various absorbent fibers. As the surgical patty is left in place, the fibers become permeated and soaked by the fluid present and are no longer absorbent and tend to adhere to the neurovascular tissues to which the gauze structure comes into contact. Another issue experienced with surgical patties is that the gauze surface must not abrade tissue as the Surgical patty is drawn across tissue.

Figure 9:
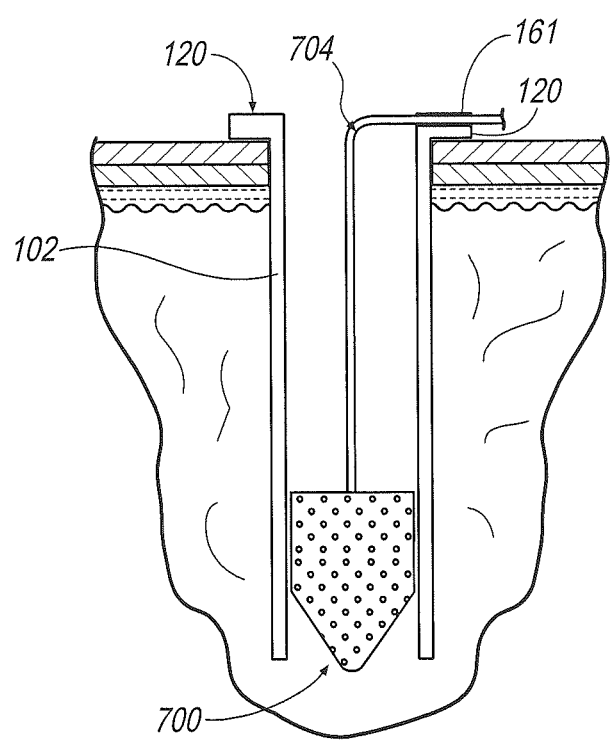
FIG. 9 is a partial cross-sectional view of the surgical access assembly with the outer sheath in place within the brain and a surgical patty inserted therein.

An exemplary configuration of a surgical patty assembly 700 that may be deployed in outer sheath 102 is shown in FIGS. 7-9. Surgical patty assembly 700 generally includes a patty body 702. A retaining cord 704 may also be provided. In one exemplary configuration, patty body 702 is configured to be relatively thin in profile such that the patty body 702 is flexible. While patty body 702 may have a variety of shapes, in one exemplary configuration, patty body 702 has a rectangular section 706 and a converging section 708. Converging section 708 may terminate in rounded tip 710 to allow for selective placement of patty body 702 in tight or constricted spaces.

Patty body 702 is defined by first and second surfaces 712, 714. First surface 712 may be constructed of a non-abrasive material that has low surface energy such that the material will not stick to tissue. For example, first surface 712 may be constructed of an elastomeric material such as silicone, polyester, polyurethane, polyethylene, high friction rubber, or similar. In one exemplary configuration, first surface 712 is constructed to be perforated with a plurality of small openings 716, as will be explained below in further detail.

Second surface 714 may be constructed of a gauze material to provide a cushioning effect so as a buffer to protect tissue from instrumentation contact and subsequent bruising, contusion or permanent damage. The gauze material may also be capable of wicking the fluid into the gauze material while not absorbing the fluid of the surgical area into the fibers of the gauze. In one exemplary configuration, a rayon gauze may be used.

As discussed above, in one exemplary arrangement, a retaining cord 704 may be provided. Retaining cord 704 may be constructed of a non-tacky material, such as polyester, such that retaining cord 704 will not adhere to tissue. An end 718 of retaining cord 704 may be bonded to the second surface 714 or in between the two surfaces of 712 and 714.

In another exemplary arrangement, a radiopaque strip 720 may be disposed on second surface 714. Radiopaque strip 720 may be used with a suitable imaging system to detect the location of patty 700 when disposed within the body of the patient.

Referring to FIG. 9, use of patty 700 will now be described. After outer sheath 102/202 is positioned within the brain, patty 700 may be positioned within outer sheath 102/202. While shown as having width that generally corresponds to the diameter of outer sheath 102/202, it is understood that patty 700 may be any size. Further, while patty 700 may be positioned within outer sheath 102/202 via surgical tweezers or other surgical tools, to facilitate removal of surgical patty 700, a free end of retaining cord 704 may be oriented to extend out of outer sheath 102, away from the area of interest.

To retain surgical patty 700 at the area of interest and to locate the retaining cord 704 out of the main surgical corridor so to prevent retaining cord 704 from encumbering the surgical corridor both physically and visually, retaining cord 704 may be engaged with separate holding member (not shown). In one exemplary arrangement, as described above, grip member 120/220 is provided with at least one retaining notch 161/261. Each retaining notch 161/261 that is configured to receive retaining cord 704 to selectively retain retaining cord 704 during the surgical procedure. Such placement makes it easier for the surgical staff to visually account for the surgical patties being used in a given procedure. In addition, such placement aids in preventing retaining cord 704 from falling into the surgical field.

During the surgical procedure, at certain times it may be necessary to suction the surgical area to remove fluid. However, great care needs to be employed in applying suction adjacent critical structures to avoid unintentional direct suctioning of such structures, which may lead to tearing or other damage. Surgical patty 700 may aid in solving this issue due to the perforations 716 formed on first surface 712. More specifically, first surface 712, is a perforated and non-abrasive material, and is positioned adjacent or directly onto the neurovascular structures. Thus perforations are also positioned against such structures. Suction may then be applied to the second side 714 of surgical patty 700, permitting fluids to be suctioned through surgical patty 700 thus allowing the passage of fluids through patty 700 due to the perforations in in 712 without absorption in second side 714. Because first surface 712 is a non-absorptive material and non-abrasive, tissue will not adhere to surgical patty 700.

Once the surgical procedure is complete, surgical patty 700 may be removed from the area of interest, and in particular, may be extracted from outer sheath 102. More specifically, retaining cord 704 may uncoupled from retaining notches 161/261 and retaining cord 704 may be pulled away from outer sheath 102/202. Because first surface 712, which is the surface that is positioned on or adjacent neurovascular tissue, is non-adhering and non-abrasive, surgical patty 700 will not unintentionally traumatize such tissue. Further, because first surface 712 is relatively smooth, it will also be non-abrasive to tissue. Thus, removal of the surgical patty will not cause trauma to such tissue or even abrade tissue during usage or removal.

It will be appreciated that the surgical access system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A surgical access system, comprising
    an outer sheath defined by an open distal end and an open proximal end and including a hollow body portion therebetween a central axis extending therethrough;
    an obturator defined by a distal end and a proximal end, wherein the distal end further comprises a tapered distal tip member;
    wherein the obturator is configured to be received within the outer sheath such that the tapered distal tip member protrudes from the open distal end of the outer sheath when the obturator is in an introducing configuration; and
    wherein the outer sheath further includes a gripping member attached to the open proximal end, wherein the gripping member has a proximal end face surface, an outer periphery, and an access opening formed through the proximal end face surface and wherein at least one retaining notch is formed on the proximal end face surface thereof such that the at least one retaining notch extends from the access opening to the outer periphery of the gripping ring and wherein at least one retaining opening is disposed through the proximal end face surface, wherein the at least one retaining opening is configured to cooperate with a fastening element to selectively secure the outer sheath within a patient.

2. The surgical access system of claim 1, wherein the gripping member includes a plurality of retaining notches.

3. The surgical access system of claim 2, wherein the plurality of retaining notches are spaced equi-distantly from one another.

4. The surgical access system of claim 1, wherein the outer sheath further comprises at least one reference element that cooperates with an imaging device to illustrate a location of the outer sheath while inserted in a body.

5. The surgical access system of claim 1, further comprising a surgical patty that is configured to be disposed through outer sheath.

6. The surgical access system of claim 5, wherein the surgical patty comprises a body member, wherein a first surface of the body member includes a non-abrasive material that will not adhere to tissue.

7. The surgical access system of claim 6, wherein the first surface includes perforations through which fluid may pass.

8. The surgical access system of claim 6, wherein the first surface is constructed of one of the following materials: silicone, polyester, polyurethane, polyethylene, and rubber.

9. The surgical access system of claim 6, wherein the body member includes a second surface that is constructed of a fluid wicking material.

10. The surgical access system of claim 9, wherein the material is rayon gauze.

11. The surgical access system of claim 9, wherein a radiopaque strip incorporated to the body member.

12. The surgical access system of claim 5, further comprising a retaining cord attached to a body member of the surgical patty.

13. The surgical access system of claim 1, wherein the at least one retaining opening includes a plurality of retaining openings that are spaced apart from one another equi-distantly.

14. The surgical access system of claim 1, wherein the at least one retaining opening is positioned adjacent a peripheral edge of the gripping member so as to be spaced from the open proximal end of the outer sheath.

15. The surgical access system of claim 1, wherein the at least one retaining opening is axially offset from the proximal end face surface of the gripping member.

16. The surgical access system of claim 1, wherein the distal end of the outer sheath includes a tapered portion that extends toward a center axis of the outer sheath.

17. The surgical access system of claim 1, wherein the distal end of the outer sheath terminates in a distal edge that surrounds the open distal end, wherein the distal edge is radiused.

18. A surgical access assembly, comprising
    an outer sheath defined by an open distal end and an open proximal end and including a hollow body portion therebetween;
    an obturator defined by a distal end and a proximal end, wherein the distal end further comprises a tapered distal tip member;
    wherein the obturator is configured to be received within the outer sheath such that the tapered distal tip member protrudes from the open distal end of the outer sheath when the obturator is in an introducing configuration; and
    wherein the outer sheath further includes a gripping member attached to the open proximal end, wherein the gripping member has a proximal end face surface, a central opening, and an outer periphery, and wherein a plurality of retaining notches are formed on the proximal end face surface thereof, each of the notches extending from the central opening to the outer periphery;
    and wherein the gripping member further includes retaining openings disposed through the proximal end face surface, wherein the retaining openings are arranged in an alternating manner with the retaining notches.

* * * * *